United States Patent [19]

Kothe

[11] Patent Number: 5,290,309
[45] Date of Patent: Mar. 1, 1994

[54] SURGICAL INSTRUMENT

[76] Inventor: Lutz Kothe, Bodmaner Str. 17, 7760 Radolfzell 14, Fed. Rep. of Germany

[21] Appl. No.: 829,481

[22] Filed: Feb. 3, 1992

[30] Foreign Application Priority Data

Apr. 19, 1991 [DE] Fed. Rep. of Germany ....... 4112818
Jul. 24, 1991 [DE] Fed. Rep. of Germany ... 9109113[U]

[51] Int. Cl.⁵ .............................................. A61B 17/28
[52] U.S. Cl. ....................................................... 606/207
[58] Field of Search ............................. 606/205–208, 606/171, 174

[56] References Cited

U.S. PATENT DOCUMENTS

| | | |
|---|---|---|
| 3,972,333 | 8/1976 | Leveen . |
| 4,712,545 | 12/1987 | Honkanen ........................ 606/208 |
| 5,176,702 | 1/1993 | Bales et al. ....................... 606/208 |

FOREIGN PATENT DOCUMENTS

| | | |
|---|---|---|
| 0279358 | 8/1988 | European Pat. Off. . |
| 450608 | 10/1991 | European Pat. Off. ............ 606/205 |
| 2802403 | 4/1979 | Fed. Rep. of Germany . |
| 2082987 | 11/1971 | France . |
| 2479680 | 10/1981 | France . |
| 2140735 | 12/1984 | United Kingdom . |

Primary Examiner—Jerome L. Kruter
Attorney, Agent, or Firm—Bachman & LaPointe

[57] ABSTRACT

A surgical instrument, in particular for endoscopy, having closable jaws comprising jaw parts such as forceps or scissor limbs which are fixed on a pull element, at least one jaw part forming an axis of rotation with the pull element and being arranged rotatably about this axis of rotation and the pull element passing through a shank tube, wherein, formed in at least one jaw part from outside is a recess, the center point (M) of which rotates about the pivot on the pull element, the recess at least partially surrounding, n the use position, an annular piece provided in the wall of the shank tube and the jaw part rotating about this annular piece during its closing or opening movement.

27 Claims, 10 Drawing Sheets

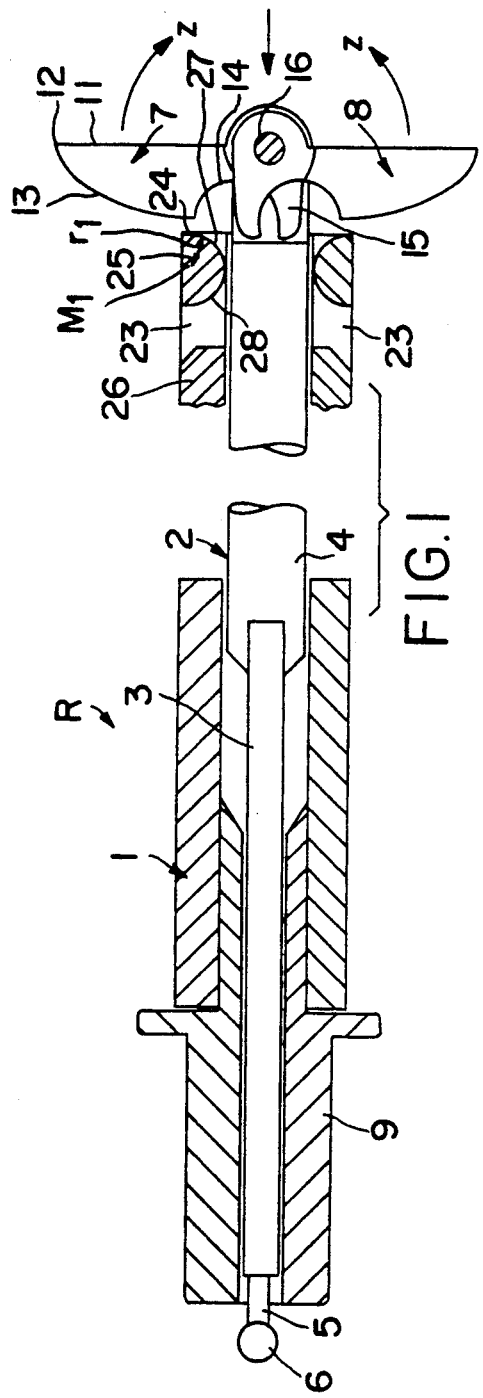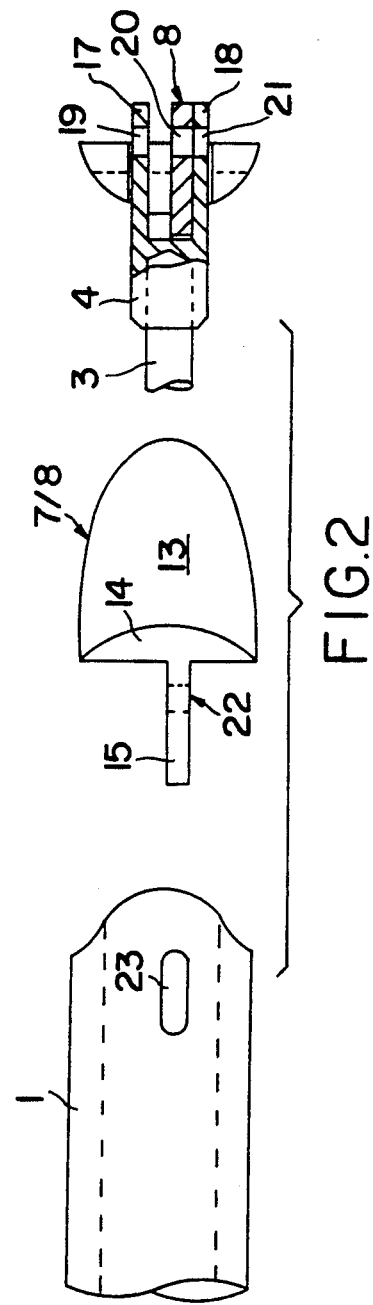

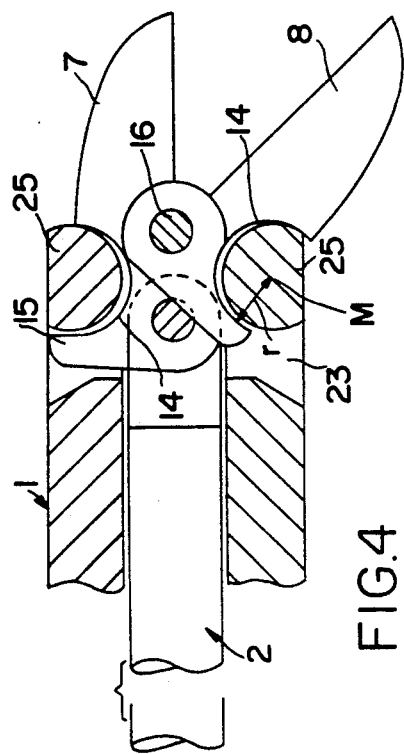
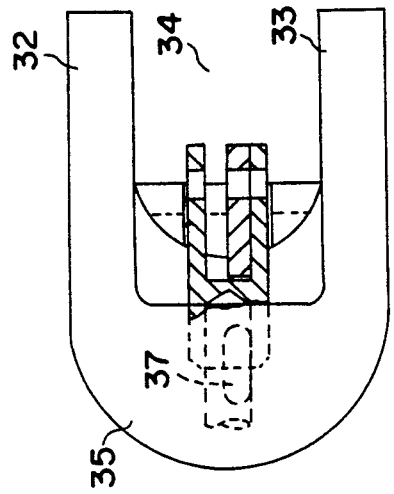
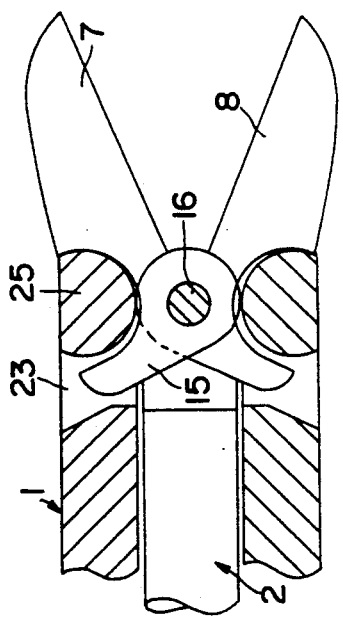
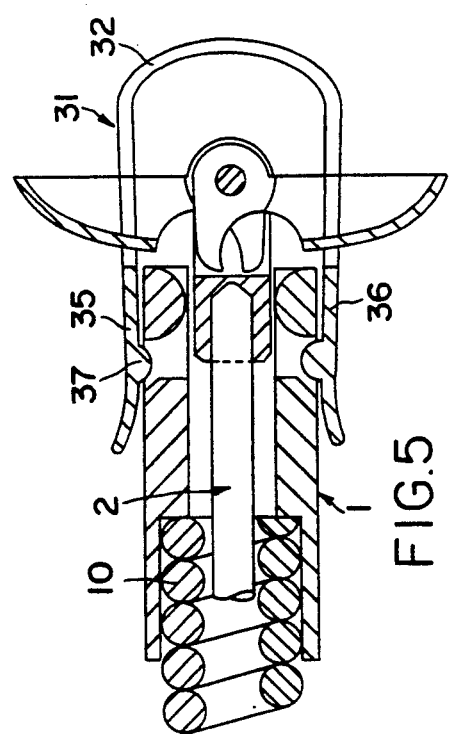

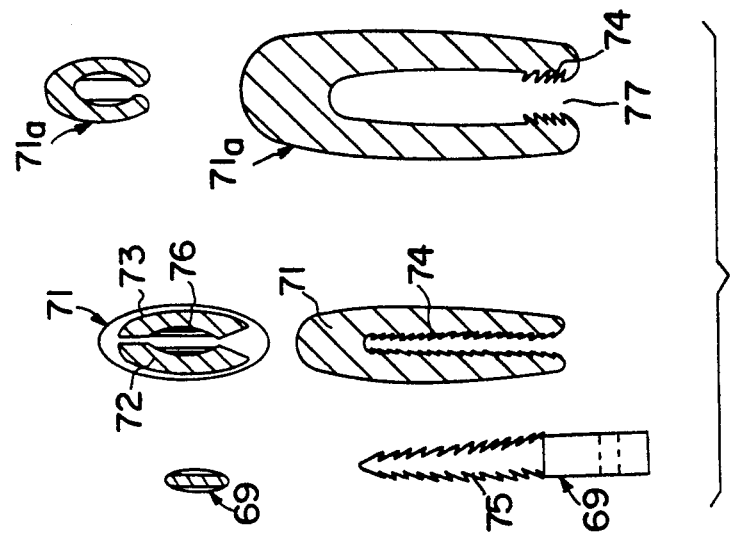
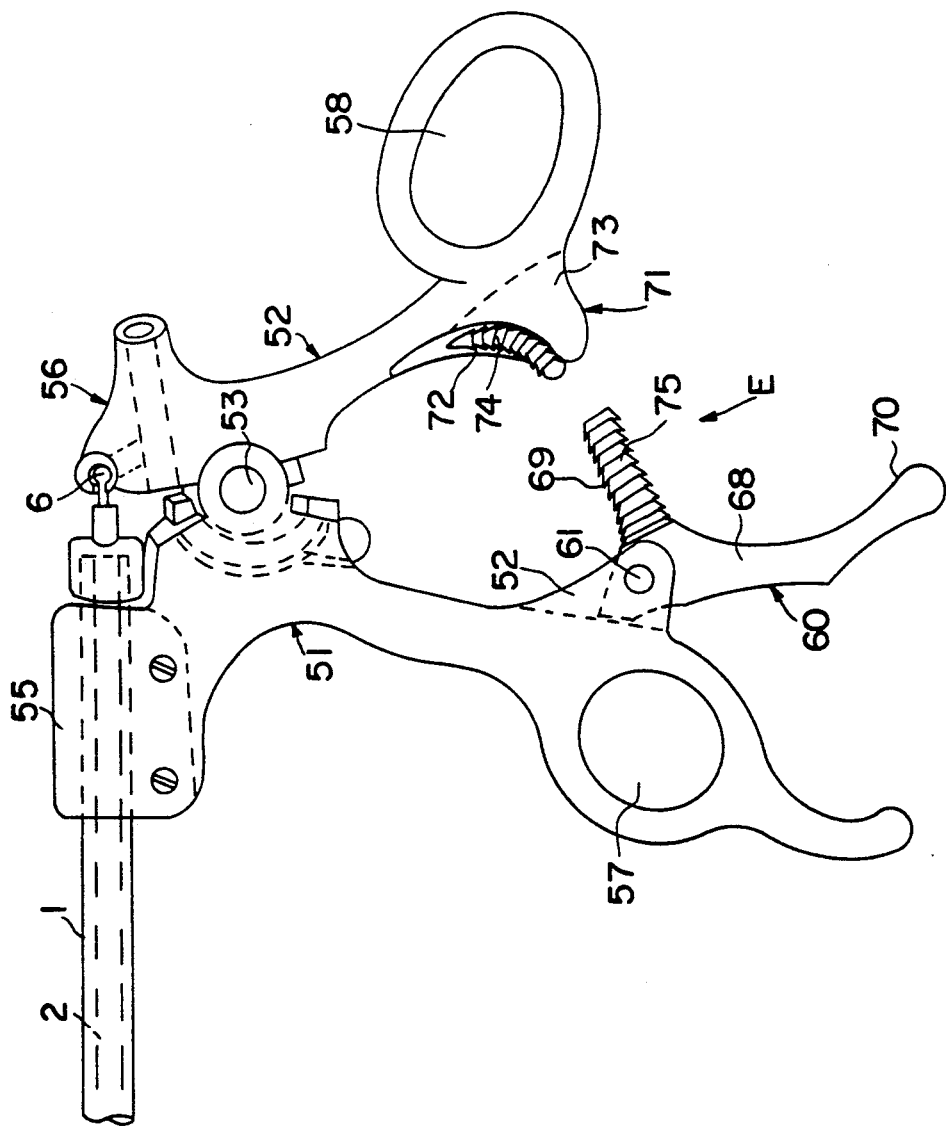
FIG.14
FIG.13

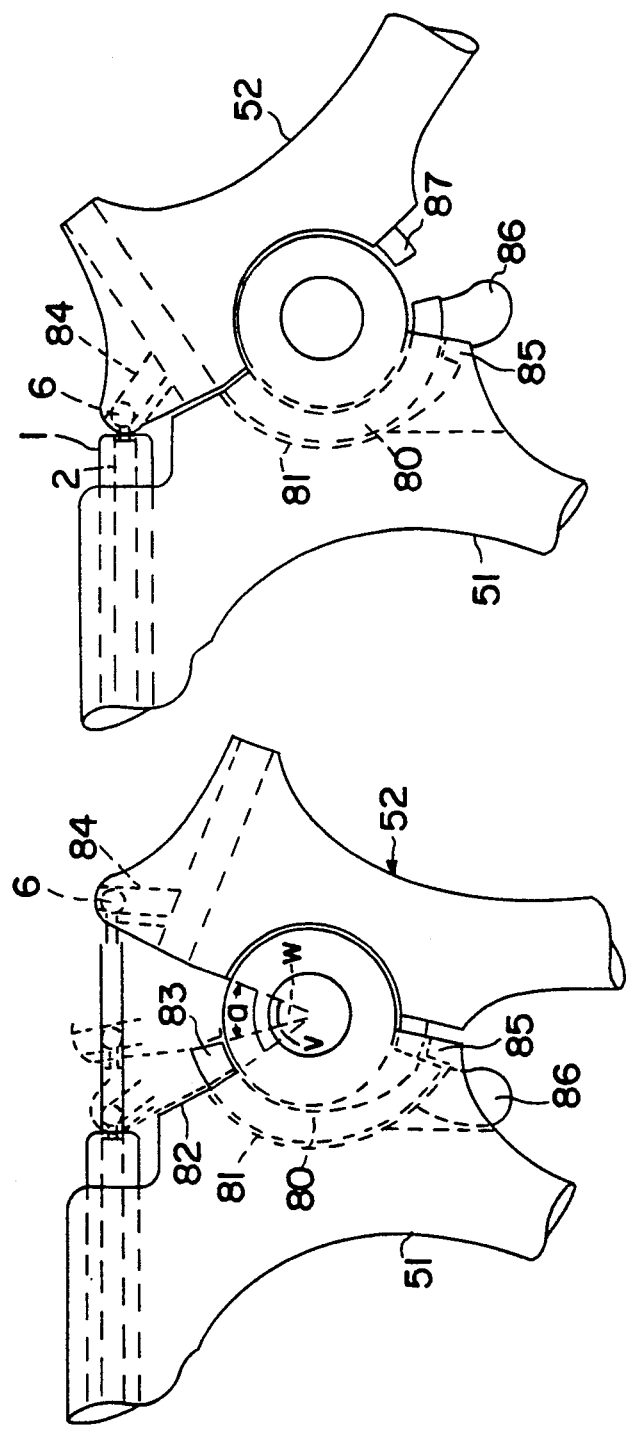

SURGICAL INSTRUMENT

BACKGROUND OF THE INVENTION

The invention relates to a surgical instrument, in particular for endoscopy, having closable jaws comprising jaw parts such as forceps or scissor limbs which are fixed on a pull element, at least one jaw part forming an axis of rotation with the pull element and being arranged rotatably about this axis of rotation and the pull element passing at least partially through a shank tube.

Surgical instruments of this kind are known in the form of forceps, scissors, clamps or the like in numerous embodiments and are used for a very wide variety of purposes. In general, they comprise two jaw parts which are moved relative to one another, clamping, cutting or shearing then being effected.

Reference is made purely by way of example to German Offenlegungsschrift 3,921,935, which discloses endoscopy forceps. Here, the forceps limbs are connected to one another via a pivot pin. Coupled to the forceps limbs on the other side of this pivot pin is a pull cable, a pull rod or the like. Connected to the pull cable is a guiding element which has at least one guiding channel in which there engages a lever extension which is formed on a forceps limb on the far side of the pivot pin or of a pivot. If a pull is exerted on this guiding element, the jaws formed by the forceps limbs close or open.

A particular disadvantage of these hitherto known forceps is the fact that they can be disassembled, cleaned and sterilized after use only with considerable trouble. Assembly in turn also requires a large amount of time and is associated with touching the parts, which are per se to be kept sterile.

In addition, in the case of many surgical instruments of this kind, the mechanism leaves much to be desired, especially as regards the transmission of force to the jaw parts.

German Utility Models 87 12 328.2 and 88 14 560.3 furthermore disclose endoscopy forceps in which the jaw parts form an axis of rotation with the pull element. These jaw parts are guided in corresponding wall openings in the shank tube, but this is very imprecise. The transmission of force for opening and closing the jaws also leaves much to be desired. In addition, the upper sleeve has to be unscrewed from the spiral for the purpose of cleaning.

The underlying object of the present invention is to provide as perfect a mechanism as possible in combination with optimum transmission of force to the jaw parts, with disassembly of the surgical instrument at the same time being extremely easy and taking little time.

SUMMARY OF THE INVENTION

Leading to the achievement of this object is the fact that formed in at least one jaw part from outside is a recess, the center point of which rotates about the axis of rotation on the pull element, the recess at least partially surrounding, in the use position, an annular piece provided in the wall of the shank tube and the jaw part rotating about this annular piece during its closing or opening movement.

The interplay between the annular piece in the shank tube and the recess is particularly important. As soon as the pull element moves in the shank tube, this axial motion is converted into a rotary motion of the jaw part or parts by the recess sliding around the annular piece. Thus at least parts of the recess always slide along the walls of the annular piece.

To ensure that movement of the jaw part to one side is not the only possibility, the recess should be of approximately semicircular design. In the event of a pull on the pull element, the jaw part is as a result closed, while, in the opposite direction, the jaw part is opened.

To ensure a good interplay between the annular piece and the recess, the radius of the recess should be only slightly larger than the radius of the annular piece. Thus, in the use position, both the center point of the recess and the center point of the annular piece are close together, giving maximum surface contact between the annular piece and the recess. This improves the guidance of the jaw part.

In one illustrative embodiment of the invention, one jaw part can be designed as a fixed part, while the other jaw part moves relative to this fixed jaw part. The two are connected to one another via the abovementioned hinge pin. It is of course sufficient here if the recess is provided in the movable jaw part and if the shank tube has only one opening or one groove and only one corresponding annular piece for sliding into the recess. However, the fixed jaw part should then have a separate recess, into which the guiding limb of the movable jaw part can disappear.

In the preferred illustrative embodiments, however, both jaw parts are movable and thus of identical design, in which case two corresponding openings or grooves and two corresponding annular pieces are also arranged in the shank wall.

For the purpose of fixing the two jaw parts, a fork with two fork limbs on the pull element is then sufficient, the jaw parts being connected to the fork limbs via a corresponding pin. When the pull element is removed together with the jaw parts, the guiding limbs can enter the region between the fork limbs due to the design of the recess, with the result that they do not interfere during the removal of the pull element. This pull element, together with the jaw parts, can thus be sterilized and cleaned separately from the shank. Cleaning of the interior of the shank is also possible in a simple manner at the same time.

Assembly is in turn accomplished in a simple manner by arranging the two jaw parts approximately horizontally. In the process, the guiding limbs disappear again between the fork limbs and the pull element can be inserted into the shank tube together with the jaw parts. As the annular pieces slide into the recess, the guiding limbs are then swiveled out of their concealed position again and slide into the opening, the jaw parts rotating about the pin or hinge pin.

The annular piece can moreover also have a different design. It is, for example, possible here for a pivot pin to be inserted in a blind slot-like recess.

To ensure that centering takes place immediately as the jaw parts are inserted into the shank tube, the guiding limbs thus finding the openings, a guide clip 31, which can be placed on the shank tube, is provided according to the invention. In the present illustrative embodiment, this guide clip comprises two open hoops which are connected to one another via snap-in strips. The jaw parts are accommodated between the hoops. The snap-in strips in turn have snap-in knobs, the position of which coincides axially with the guiding limbs. These snap-in knobs then clip into the openings, with the result that the guiding limbs find the opening from the interior of the shank in all cases. This is a preferred embodiment of the invention.

Another possibility for centering or facilitating the insertion of the jaw parts into the shank tube consists in the presence on the pull element of a plunger piece into which at least one guiding groove is formed. This guiding groove then interacts with a corresponding guiding projection in the shank tube during the insertion of the plunger piece into the shank tube. An anti-rotation safeguard is thereby provided at the same time.

Overall, the surgical instrument is of extremely simple construction and easy to operate. It allows high transmission of force to the jaw parts, improving the cutting effect. Particularly to be emphasized is the ease of disassembly. For this purpose, all that is required is for the pull element to be released from a corresponding forceps or scissor handle or the like.

This purpose is also served especially by a further embodiment of the invention. To move the two jaw parts, corresponding forceps limbs are provided which can be opened and closed by the human hand. The shank tube is fixed on one forceps limb, generally in a holding device, while the pull element is in general connected to the other forceps limb. In the present illustrative embodiment, the pull element has a driving ball which, in the use position, rests in a ball socket in a neck of this forceps limb. Both forceps limbs then rotate about a common pivot.

To allow the pull element to be released in a simple manner from its forceps limb but, on the other hand, to ensure that it does not slide out of its holding device in the case of a normal actuation of the surgical instrument, a catch device should be provided which limits the motion of the two forceps limbs relative to one another. The limitation of the motion has the effect that, in the case of normal actuation of the forceps, the driving ball remains in the ball socket in each end position but that, when this catch device is released, one forceps limb can be swiveled sufficiently far for the driving ball simply to slide out of the ball socket and to allow the pull element then to be pulled out of the shank tube together with the jaw parts.

In a preferred embodiment, this catch device essentially has a semicircular arch which likewise rotates about the pivot of the two forceps limbs. To accommodate it, a guiding channel, in which the semicircular arch slides, is formed in one forceps limb. In one end position, in which the motion of the two forceps limbs relative to one another is to be limited, the semicircular arch protrudes with a stop stud beyond a stop face, with the result that a forceps limb can only be moved as far as this stop stud. If, however, the position of the semicircular arch is altered, this stop stud disappears in the forceps limb, i.e. the forceps limb can be swiveled as far as the stop face, it being possible, in this end position, for the driving ball to slide out of the ball socket.

In its end position in which it projects with a stop stud beyond the stop face, the semicircular arch should preferably be fixed releasably. This is accomplished in a simple manner by the semicircular arch engaging in this end position behind a latching heel provided in the forceps limb. The semicircular arch can be pushed out of this latching-heel bearing simply by exerting pressure on a tab or the like on the semicircular arch, it then being free and able to rotate about the pivot.

The present invention is also concerned with a further embodiment of the forceps limbs or their fixing relative to one another, this being a preferred embodiment for use with the surgical instrument under consideration. However, it is not the intention to restrict the present invention solely to this use; on the contrary, the embodiment described below of a locking device is transferable to many surgical instruments which operate with forceps or scissor handles.

The inventive idea relates particularly to the possibility of fixing the forceps limbs in a particular relationship relative to one another.

Locking devices are known for this purpose, two locking strips being, for example, secured on each limb and overlapping/underlapping each other, the respective teeth being in engagement with one another. It is disadvantageous here that a second hand is necessary to release the locking device.

Another locking device comprises a locking strip which is connected in articulated fashion on one side to one forceps limb and, on the other side, is pressed against a latching tooth on the other forceps limb by a spring. If it is assumed that the user operates the forceps or scissors with his thumb and index finger, this locking device can only be released with the other hand.

Other locking devices are either difficult to operate or are of very complicated construction.

The further embodiment of the invention under consideration develops a forceps or scissor handle in which the locking device is of very simple construction and, in particular, is very easy to actuate with just one hand, more specifically with the hand which also actuates the forceps or scissor handle itself.

This purpose is served by the fact that, adjoining the locking strip, there is a lever limb, if required with a finger hollow.

The rotation of the locking strip which brings the locking teeth out of engagement with the engagement tooth can be effected by means of one finger of the actuating hand which is also holding the forceps or scissor handle. In general, this will be done by means of the middle finger, ring finger or little finger.

The locking strip should preferably be under the pressure of an energy accumulator, the pressure having the effect that the locking strip remains in engagement with the engagement tooth. This means that, to release the locking device, the user has to perform just one movement of one finger in one direction. The engaging movement is then taken over by the energy accumulator.

The locking strip can rest against the forceps limb having the engagement tooth or engage round it. Preferably, however, a slot is formed in the forceps limb, through which slot the locking strip engages. The locking strip thereby presents the least interference with the normal action of the forceps or scissor handle. In addition, the locking strip is thereby provided with more reliable guidance.

If the locking strip engages on the forceps limb from outside, an additional engagement tooth is formed on the forceps limb there. If, however, in the preferred illustrative embodiment, the locking strip engages through the forceps limb, then it is sufficient if one slot edge is formed like a wedge at that point to give an engagement tooth.

Another idea is that of a clamp-shaped receiver for the locking strip on the other forceps limb, into which receiver the locking strip engages.

For mounting the locking strip on the other forceps limb, the intention is to use a simple hinge pin about which the locking strip can rotate. To ensure favorable engagement of the energy accumulator designed as a spring strip, the articulation should be effected by means of a hook-shaped formation which forms an engagement hollow between itself and the actual locking strip, into which hollow the energy accumulator can engage and press against the hook. In a preferred illustrative embodiment, the energy accumulator is designed as a simple spring strip which lies firmly on an inner face of the forceps limb. A front face of the hook is then supported against this spring strip above the hinge pin, the locking strip thus being under a prestress towards the engagement tooth.

Further advantages, features and details of the invention emerge from the following description of preferred illustrative embodiments and with reference to the drawing; the latter shows in

BRIEF DESCRIPTION OF THE DRAWINGS

FIG. 1 a longitudinal section through a surgical instrument according to the invention;

FIG. 2 an exploded representation of parts of the surgical instrument according to FIG. 1, shown partially cut away;

FIG. 3 a longitudinal section through a part-region of the surgical instrument according to FIG. 1, in another use position;

FIG. 4 a longitudinal section through a part-region of the surgical instrument according to FIG. 1, in two different use positions;

FIG. 5 a partially depicted longitudinal section through a further illustrative embodiment of the surgical instrument according to FIG. 1;

FIG. 6 a detail of FIG. 5, turned through 90 degrees and shown partially cut away;

FIG. 13 a plan view of a forceps or scissor handle according to the invention in the open position;

FIG. 14 cross sections through various embodiments of latching elements;

FIG. 17 shows an enlarged plan view of a part-region of the forceps or scissor handle according to the invention and corresponding to FIG. 13;

FIG. 18 an enlarged plan view of the part-region of the forceps or scissor handle in accordance with FIG. 17, in another use position;

DETAILED DESCRIPTION OF PREFERRED EMBODIMENTS

Figure 7:
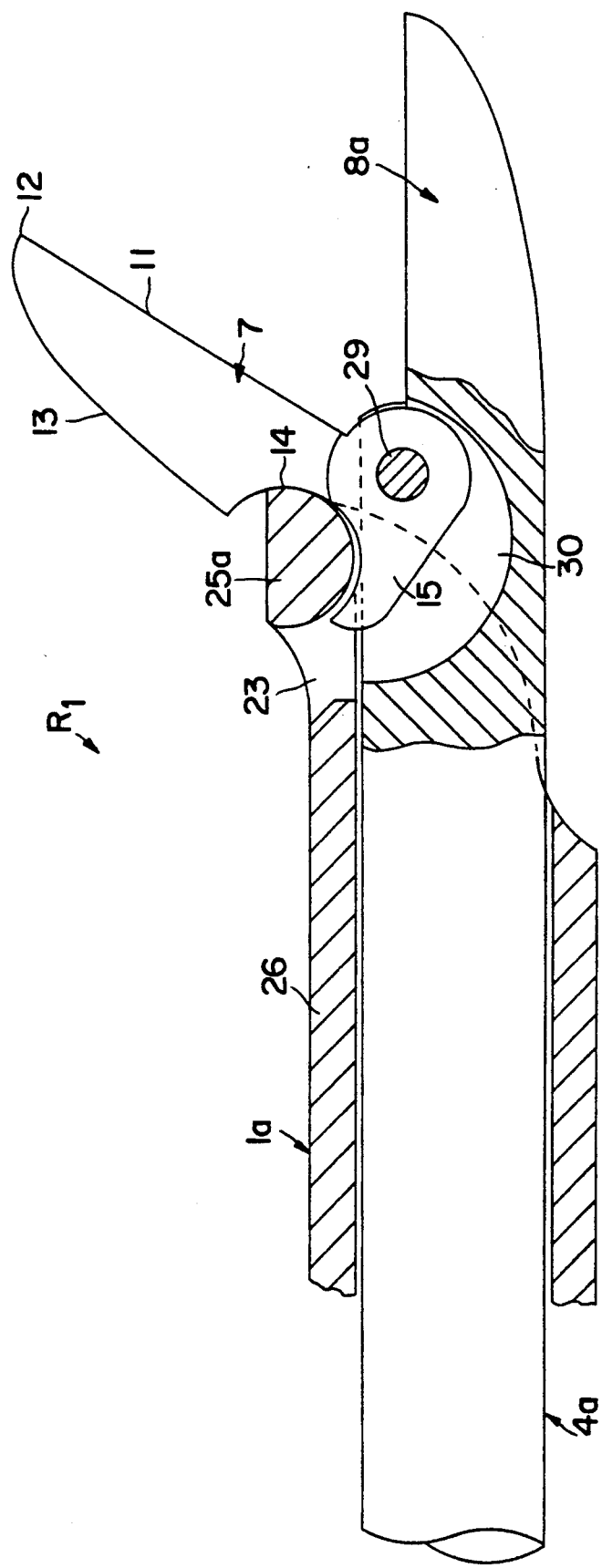
FIG. 7 a partially depicted longitudinal section through a further illustrative embodiment of a surgical instrument according to FIG. 1.

A surgical instrument R according to the invention, such as, for example, forceps or scissors for endoscopy, has a shank tube 1 in which a pull rod 2 is guided. In the present illustrative embodiment, the pull rod 2 is essentially composed of a rod 3 and a plunger piece 4, the plunger piece 4 having a larger diameter than the rod 3. Integrally formed on the rod 3 at one end, via a connection piece 5, is a driving ball 6, while, at the other end, two movable jaw parts 7 and 8 are mounted in the plunger piece 4. Instead of the jaw parts 7 and 8, it is also possible for scissor parts, forceps limbs or similar instrument parts to be fixed here.

The driving ball 6 serves for connection to a scissor or forceps handle of known design, in which case the driving ball 6 rests in a corresponding recess of the scissor part and the connection piece 5 reaches through a slot. Of this scissor handle, the figure also shows a further guiding piece 9, through which the rod 3 likewise passes.

Numerous embodiments both for the guiding piece 9 or the entire scissor part and for the pull rod 2 are conceivable and known and are intended to be encompassed by the present invention. It is, for example, also possible for the rod 3 to be replaced by a flexible pull cable. It can furthermore be seen in FIG. 5 that springs 10 can be arranged in the shank tube 1 for the purpose of returning the pull rod 2. As stated, numerous embodiments are known here.

Essential in the context of the present invention, on the other hand, is the configuration of the jaw parts 7 and 8, their arrangement and connection on the plunger piece 4 and the front region of the shank tube 1 for guiding these jaw parts 7 and 8. Each jaw part 7, 8 has a cutting or clamping edge 11, which can be denoted in general terms as the working edge. Adjoining the tip 12 of the jaw part 7, 8 there is then a curved rear wall 13, into which is formed a semicircular recess 14. By virtue of this semicircular recess 14, a guiding limb 15 is formed which will be described in greater detail subsequently.

In the region of their guiding limb 15 or next to the semicircular recesses 14, both the jaw parts 7 and 8 are connected to the plunger piece 4 via a pin 16, for which purpose, as shown in FIG. 2, a fork consisting of two fork limbs 17 and 18 is provided in the plunger piece 4. These two limbs 17 and 18 accommodate the jaw parts 7 and 8 between them, the pin 16 then merely having to be inserted through the corresponding articulation holes 19, 20 and 21 of the limbs 17, 18 and jaw parts 7, 8.

FIG. 2 furthermore shows a rear view of a jaw part 7, which is to be regarded merely as an illustrative embodiment. Here, the jaw part 8 is of essentially half shell-shaped design, a partially hemispherical rear wall 13 thus being formed. Adjoining this is the recess 14, although, towards the guiding limb 15, the said recess is only provided in the region of a connection strip 22.

In FIGS. 1 and 2, it can furthermore be seen that there are openings 23 on both sides in the shank 1, the said openings serving to receive the guiding limb 15, as mentioned below. Towards one shank-tube rim 24, the openings 23 are bounded by an annular piece 25, which is semicircular as seen in cross section and is formed in the appropriate shape from the wall 26 of the shank tube 1. Towards the shank-tube rim 24, this annular piece 25 forms a funnel-shaped draw-in wall 27, while, likewise widening in a funnel shape, it opens up the opening 23 by means of a corresponding sliding edge 28.

The present invention functions as follows:

For cleaning purposes or for disinfection, the driving ball 6 or a similar holding device is released from the corresponding handle part and the pull rod 2 is pulled out of the connection piece 9 and the shank tube 1 together with the jaw parts 7 and 8. The interior of the shank tube and the pull rod 2 together with the jaw parts 7 and 8 can now be thoroughly cleaned throughout.

For the purpose of assembly, the pull rod 2 is reinserted into the shank tube 1 and the guiding piece 9, the jaw parts 7 and 8 being in the use position shown in FIG. 1. During this process, the guiding limbs 15 of both jaw parts 7 and 8 disappear between the fork limbs 17 and 18, allowing them to reach through between the annular pieces 25.

As soon as the guiding limbs 15 of both jaw parts 7 and 8 are within the clear width of the annular pieces 25, the rear wall 13 of each jaw part 7 and 8 strikes the shank-tube rim 24, with the result that the jaw parts 7 and 8 are moved in the closing direction z. The recess 14 of each jaw part 7 and 8 here opens towards the corresponding annular piece 25, the draw-in wall 27 sliding into the recess 14, while the guiding limb 15 slides onto the sliding edge 28 and enters the opening 23. These different use positions are depicted in stages in FIGS. 3 and 4. The way in which the annular piece 25 engages in the semicircular recess 14 can be seen in FIG. 4, at the bottom. The recess at least partially surrounds the annular piece 25.

In another use position in accordance with FIG. 3, the guiding limbs 15 have already been largely retracted into the openings 23 and the jaw parts 7 and 8 are on the way to a closed position. This closed position is shown finally in FIG. 4, at the top, for one jaw part 7. In this position, the guiding limb 15 rests in the opening 23, while the annular piece 25 presses on the jaw part 7 in the recess 14. This results in a very favorable force distribution.

In a further illustrative embodiment R1 of the invention in accordance with FIG. 7, a jaw part 8a is formed integrally on the corresponding plunger piece 4a. This fixed jaw part 8a is connected via a hinge pin 29 to the movable jaw part 7, which is designed as described above. To enable the fixed jaw part 8a to accommodate at least the guiding limb 15 of jaw part 7, a recess 30 is formed in the fixed jaw part 8a.

In this illustrative embodiment, only one opening 23 for a guiding limb 15 need be provided in the wall 26 of the shank tube 1a. For this reason, too, only one annular piece 25a is formed here towards the shank-tube rim 24.

When the plunger piece 4a is pulled out, the guiding limb 15 disappears into the recess 30 and thus does not form an obstacle to removal. Upon insertion, on the other hand, the annular piece 25a makes contact in the recess 14, with the result that the recess 14 surrounds this annular piece 25a, the guiding limb 15 moving into the opening 23 and the jaw part 7 being rotated about the hinge pin 29.

It has been found in practice that finding the openings 23 presents difficulties particularly when using flexible pull cables instead of a rigid pull rod 2. In order to counter this disadvantage, a guide clip 31 is placed on the shank tube 1 in accordance with FIGS. 5 and 6. By mean of two open hoops 32 and 33, this guide clip 31 forms an open, U-shaped space in which the jaw parts 7 and 8 can move. Both hoops 32 and 33 are connected to one another by means of snap-in strips 35 and 36, a snap-in knob 37, which can snap into the opening 23, being formed on each snap-in strip 35 and 36 towards the inside. The guide clip 31 is thereby fixed in its position, with the result that the jaw parts 7 and 8 too are guided into the space 34 in a precise manner in relation to the shank tube 1. Since the snap-in knobs 37, like the guiding limbs 15 are situated eccentrically, it is in this way ensured that the guiding limbs 15 engage in the openings 23 and, in the process, displace the snap-in knobs 37 from the openings 23, allowing the guide clip 31 to be removed.

Figure 8:
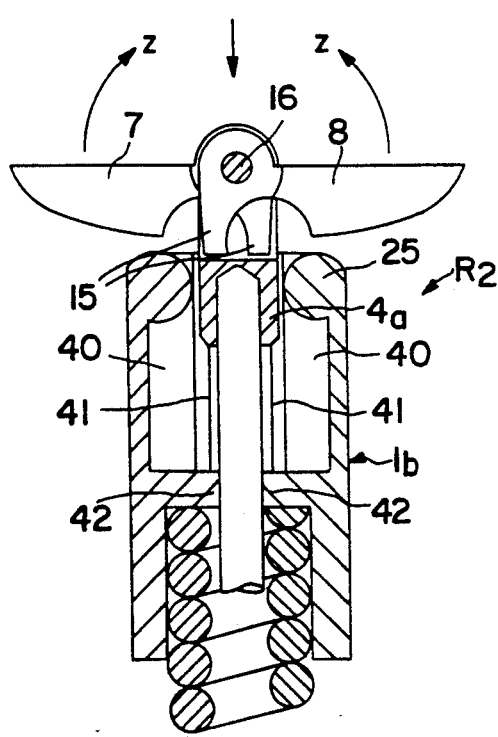
FIG. 8 a longitudinal section through a part-region of a further illustrative embodiment of a surgical instrument.

In the further illustrative embodiment of a surgical instrument R2 according to the invention and in accordance with FIG. 8, it can be seen that a corresponding shank tube 1b does not have any openings 23 for the corresponding guiding limbs 15. The shank tube 1b is thus an outwardly closed sleeve, thus making it impossible for dirt, remains of fabric or blood to collect in an opening.

To ensure nevertheless that the jaw parts 7 and 8 interact in corresponding fashion with the annular pieces 25, grooves 40 are formed in the shank tube 1b from inside, into which grooves the guiding limbs 15 can engage. At the same time, it is of course conceivable for the guiding limbs 15 to be of considerably shorter design than that illustrated.

It is furthermore possible, in FIG. 8, instead of the above-described guide clip 31 for some other centering means or guidance of a plunger piece 4a to be provided, allowing a guide clip 31 to be dispensed with. The plunger 4a is designed as an extended sleeve, guiding grooves 41 being formed in it on both sides from outside. Engaging in these guiding grooves 41 are guiding projections 42 which are formed on the inside of the shank tube 1b. Together with the guiding grooves 41, these guiding projections 42 have the effect of centering the plunger piece 4a and hence also the jaw parts 7 and 8. They also provide an anti-rotation safeguard.

Figure 9:
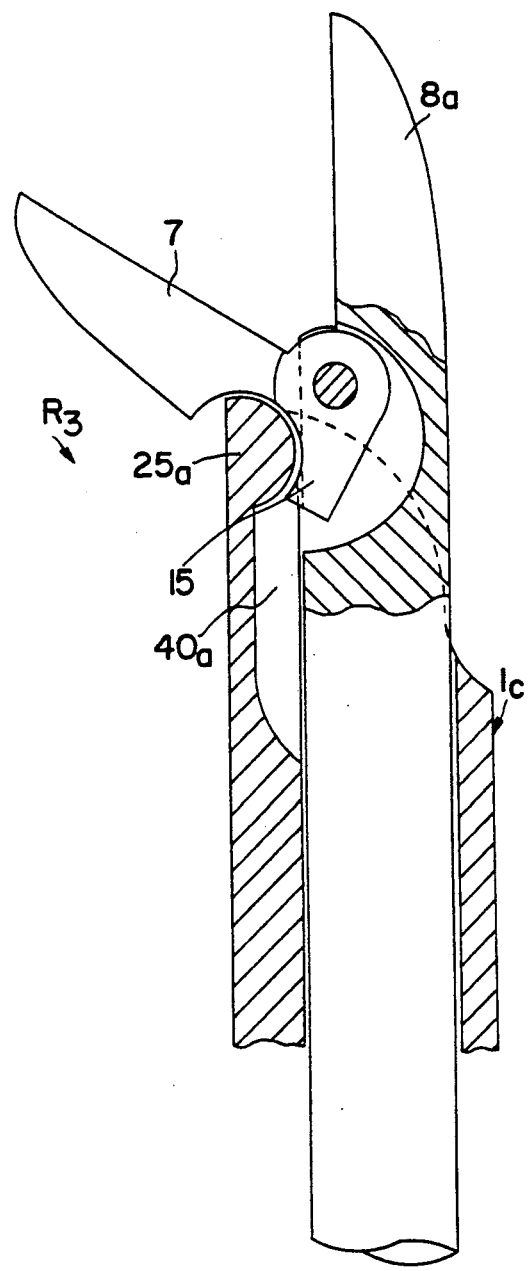
FIG. 9 a partially depicted longitudinal section through a further illustrative embodiment of a surgical instrument similar to that in FIG. 7.

The further embodiment R3 of a surgical instrument according to the invention and in accordance with FIG. 9, merely shows that, here too, a shank tube 1c does not have an opening, as was still provided in accordance with FIG. 8. Instead, here too, a groove 40a, into which the guiding limb 15 can slide, is formed in the shank tube 1c from the inside behind the annular piece 25a.

Figure 10:
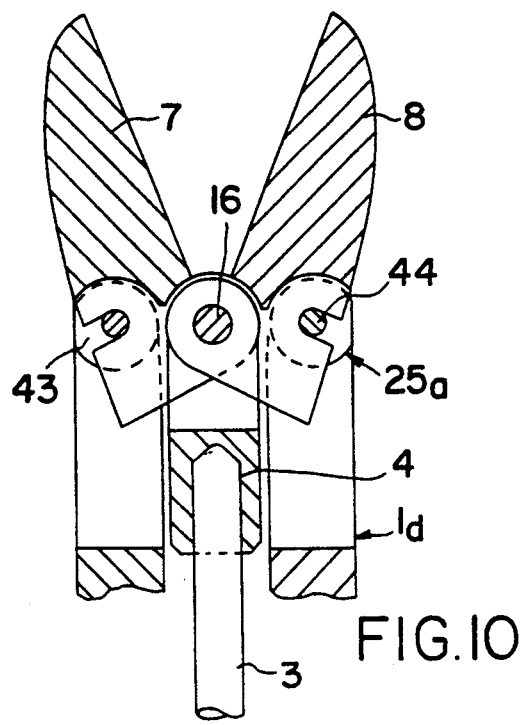
FIG. 10 a longitudinal section through a part-region of a further illustrative embodiment of a surgical instrument.
Figure 11:
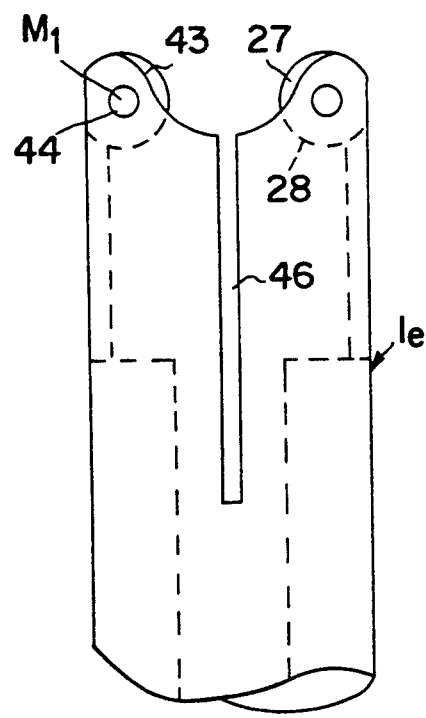
FIG. 11 a plan view of a part of the surgical instrument according to FIG. 10.
Figure 12:
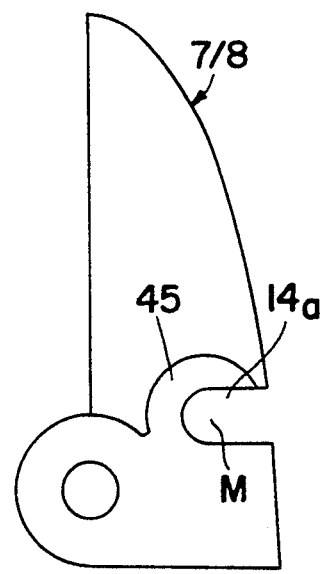
FIG. 12 a plan view of a jaw part of the surgical instrument according to FIG. 10.

FIGS. 10 to 12 relate to another configuration of the jaw parts 1 and their guidance on an annular piece 25a. Although, here too, the annular piece 25a has a draw-in wall 27 and a sliding edge 28, each annular piece 25a is provided with two disk-shaped elements 43, between which is arranged a pivot pin 44 of considerably smaller diameter.

In the use position, this pivot pin 44 rests in a recess 14a, which is designed as a blind slot. The base of this recess 14a is likewise semicircular, with the result that, here too, a center point M is formed which, in the use position, coincides approximately with a center point M1 of the pivot pin 44.

In the use position, the disk-shaped elements 43 also rest in corresponding cut-outs 45 of the jaw parts ƒ and rotate in the latter. Good support is thereby provided for the jaw parts ƒ.

In FIG. 11, it can furthermore be seen that an expansion joint 46 is cut into the shank tube 1d, compensating any inaccuracies of fit.

According to FIG. 13, a forceps or scissor handle according to the invention, for a surgical instrument R, has two forceps limbs 51 and 52, which are connected to one another in articulated fashion at a pivot 53. An opening and closing movement is performed about the pivot 53. Forceps or scissor handles of this kind are also used in the case of surgical instruments such as those indicated in European Patent 0,279,358. In general, there is, adjoining a corresponding holding device 55 of the forceps limb 51, a working device proper of the surgical instrument, in particular the shank tube 1, through which the pull rod 2, which is connected via the driving ball 6 to a neck 56 of the other forceps limb 2, then passes.

In the present illustrative embodiment, gripping lugs 57 and 58 are formed on each forceps limb 51 and 52, respectively, for the actuation of the forceps limbs 51 and 52, i.e. for carrying out the opening and closing movements in the direction of the double arrow 54. Instead of the gripping lugs 57 and 58, it is also possible, for example, for simple gripping grooves or the like to be provided on the forceps limbs 51 and 52.

It is essential that the forceps limbs 51 and 52 can be fixed at a distance from one another by a locking device E. This locking device E has a lever 60, which is pivotably connected to forceps limb 51 via a hinge pin 61. For this purpose, two tabs 52 are formed on forceps limb 51, the said tabs surrounding the lever 60 like a clamp.

The locking strip 69 is assigned to a receiver 71, which is situated on the other forceps limb 52. In this illustrative embodiment in accordance with FIG. 13, the receiver comprises two clamp strips 72 and 73, which are formed on forceps limb 52, preferably integrally. Formed in the inside wall of the two clamp strips 72 and 73 there are in each case latching teeth 74 which interact with corresponding latching teeth 75 on the outer surface of the locking strip 69.

The forceps or scissor handle according to the invention functions as follows:

For free movement of the two forceps limbs 51 and 52, the locking device E is released by swivelling the locking strip 69 out of the engagement range of the receiver 71 via the lever 60. The latching teeth 74 are out of engagement with the latching teeth 75. The lever 60 is held in the corresponding position by the user, and, for example, the little finger of the user can rest in the finger hollow 70.

If the forceps limbs 51 and 52 are to be fixed in a particular relationship relative to one another, the user brings the locking strip 69 into a position in which it can enter the receiver 71. In this process, the latching teeth 75 engage in the latching teeth 74. If required, this locking can be canceled again by a corresponding pressure on the lever limb 68.

A plan view of and a cross section through the locking strip 69 is shown in FIG. 14. Next to it, in cross section, is to be seen the receiver 71 and, in particular, also the latching teeth 74. Depicted above this is a cross section through the receiver 71, and discernible, in particular, is an oval internal shape which guarantees better guidance of the locking strip 69, which is oval in cross section.

In a further illustrative embodiment, it is also possible for a receiver 71a to be covered with a small number of latching teeth 74 only after a receiving opening 77. The corresponding cross section is likewise depicted above it in FIG. 14.

Figure 16:
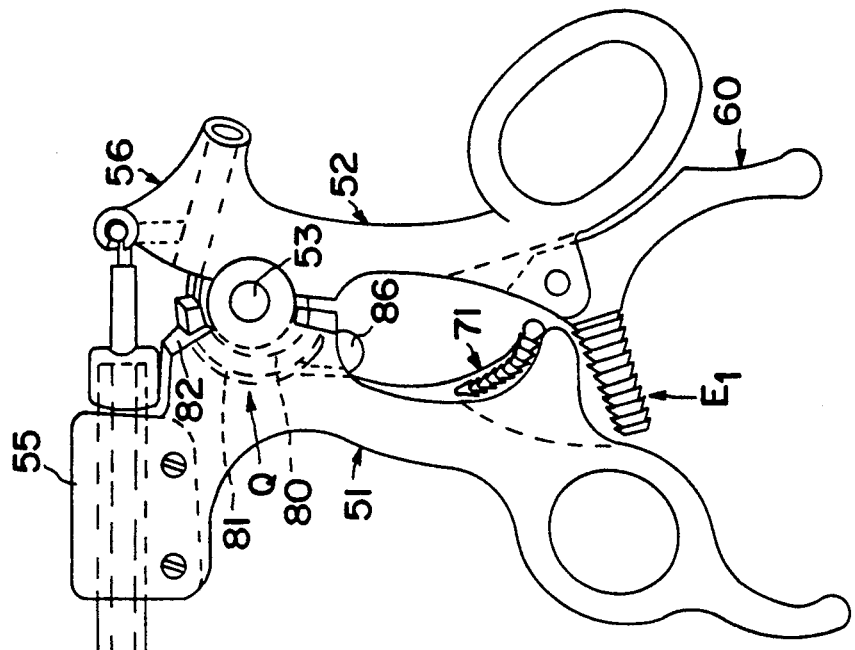
FIG. 16 a plan view of the illustrative embodiment of the forceps or scissor handle according to the invention and in accordance with FIG. 15, in another use position.
Figure 15:
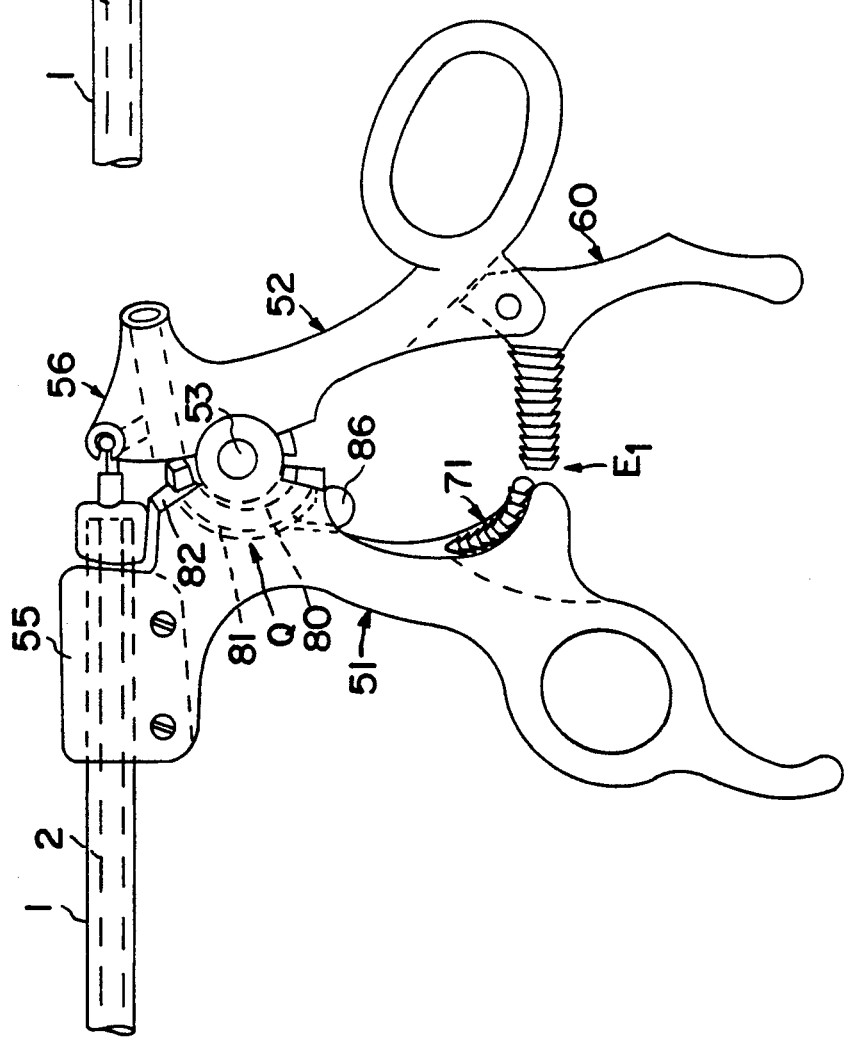
FIG. 15 a plan view of a further illustrative embodiment of a forceps or scissor handle according to the invention in the open position.

FIGS. 15 and 16 make it clear that the locking device E1 can also be arranged in reverse, that is to say that the lever 60 is situated on forceps limb 52 and the receiver 71 is situated on forceps limb 51. This embodiment too is also intended to be encompassed by the inventive idea since it is equivalent to the embodiment shown in FIG. 13.

However, also depicted in FIGS. 15 to 18 is a particularly preferred catch device Q which guarantees, on the one hand, that, during the movement of the forceps limbs 51 and 52, the connection of the pull rod 2 at the neck 56 is retained but, on the other hand, that this connection can be released in a simple manner so that removal of the pull rod from the shank tube 1 and hence cleaning of the corresponding parts is very easily possible.

For this purpose, the catch device Q preferably has a semicircular arch 80 which is arranged around the pivot 53. This semicircular arch 80 can also be moved around this pivot 53 in a corresponding guiding groove 81, although, as shown in FIG. 17, it can be fixed in a particular use position. In this use position, a stop stud 83 protrudes as part of the semicircular arch 80 from a stop face 82 of the forceps limb 51 and thus limits a rotary motion of the forceps limb 52 to an angle w. This angle w is designed such that the driving ball 6 is still situated in a ball socket 84 in such a way that it cannot slide out of this ball socket 84. This is indicated in broken lines in FIG. 17. In this position, the semicircular arch 80 moreover strikes at the other end of the stop stud 83 against a latching heel 85 and is thus fixed securely against rotation.

To release the semicircular arch 80, it is raised via a tab 86, allowing it to travel over the latching heel 85, as illustrated in FIG. 18. During this process, the stop stud 83 disappears inside the guiding groove 81 and thus no longer provides a limit for the rotary motion of forceps limb 52. For this reason, forceps limb 53 can perform a motion through the angle v, the ball socket 84 moving into a position in which the driving ball 6 can slide out of the ball socket 84. The pull rod 2 can now readily be removed from the shank tube 1.

After cleaning all the parts, it is sufficient for the pull rod 2 to be pushed into the shank tube 1, the driving ball 6 then sliding readily into the ball socket 84. Forceps limb 52 is now moved towards forceps limb 51, closure of the two forceps limbs thus occurring. During this process, a return stud 87 strikes the semicircular arch 80 and pushes it together with the tab 86 into a latching position, in which the semicircular arch 80 engages behind the latching heel 85 and the stop stud 83 protrudes from the stop face 82. In the event of a now following further operation of the forceps limbs 51 and 52, it is impossible for the ball socket 84 to move into a position in which the driving ball slides out of the ball socket 84 by mistake.

The semicircular arch 80 can also optionally be arranged with the same function in forceps limb 52. Formed in a forceps limb 52a in a further illustrative embodiment of a locking device E is a recess 92 in which rests a hook 93 formed on a lever 60a. Passing through this hook 93 towards the end is a hinge pin 61a, the hook 93 furthermore forming with the lever 60a an engagement hollow 94 into which, in the use position, a spring strip 95 engages. A front face 96 of the hook 93 is supported against this spring strip 95, the spring strip 95, which is under prestress, bringing about a movement of the lever 60a in direction x. The spring strip 95, which is fixed on the forceps limb 52a via corresponding screws 97, presses on the front face 96, with the result that the lever 60a rotates about the hinge pin 61a.

If the forceps limbs 51a and 52a are to be fixed in a particular relationship relative to one another, it is sufficient for the user to release his counterpressure against the spring strip 95, with the result that this spring strip 95 can rotate the lever 60a about the hinge pin 61a and the engagement tooth 103 engages in one of the locking teeth 104. This locking can be canceled again when required by a corresponding pressure on the lever limb 68.

The hook 93 is moreover arranged in a region between the lever limb 68 and a locking strip 69. Adjoining the lever limb 68 there is furthermore the finger hollow 70.

Figure 20:
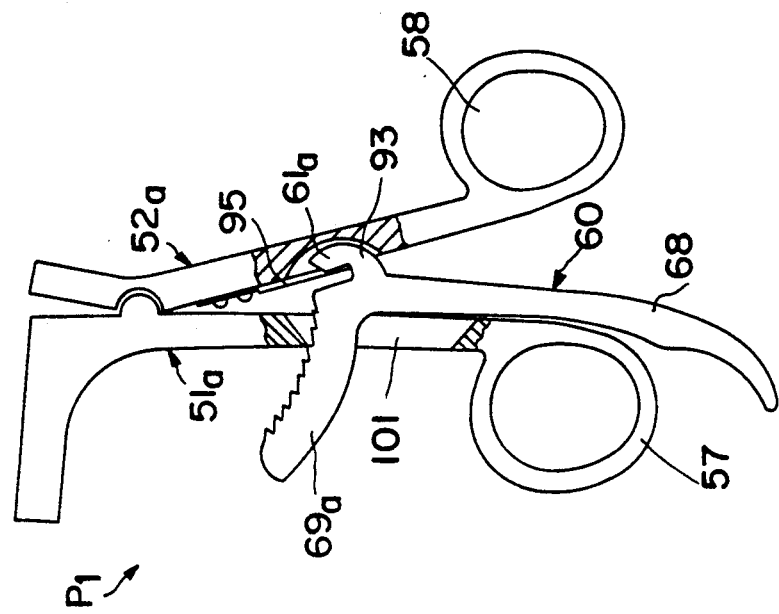
FIG. 20 a plan view of the forceps or scissor handle according to FIG. 19 but in the closed position.
Figure 19:
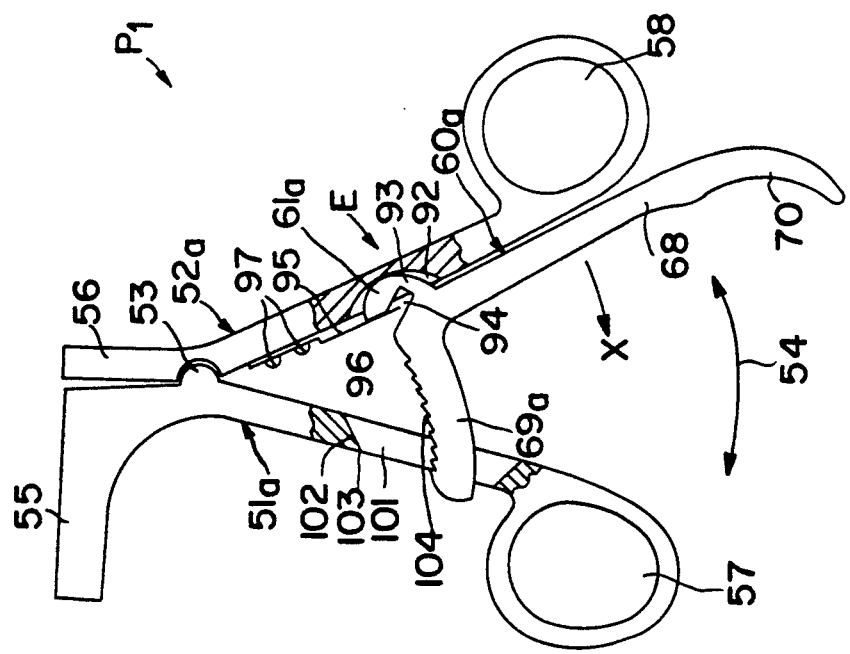
FIG. 19 shows a plan view of a further illustrative embodiment of a forceps or scissor handle according to the invention in the open position.

The locking strip 69a reaches through a slot 101 in the other forceps limb 51a, an upper slot edge 102 being of wedge-shaped design and forming an engagement tooth 103. Locking teeth 104 on the upper side of the locking strip 69a interact with this engagement tooth 103, as shown, in particular, in FIG. 20.

Figure 22:
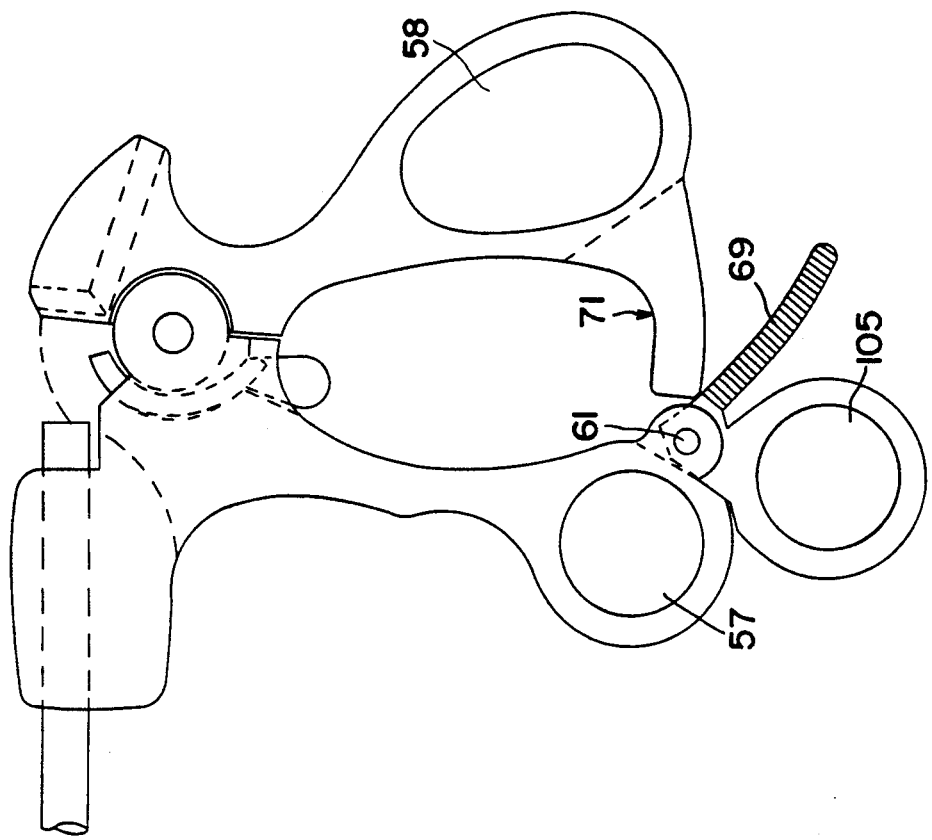
FIGS. 21 and 22 plan views of a further illustrative embodiment of a forceps or scissor handle according to the invention in accordance with FIGS. 19 and 20.
Figure 21:
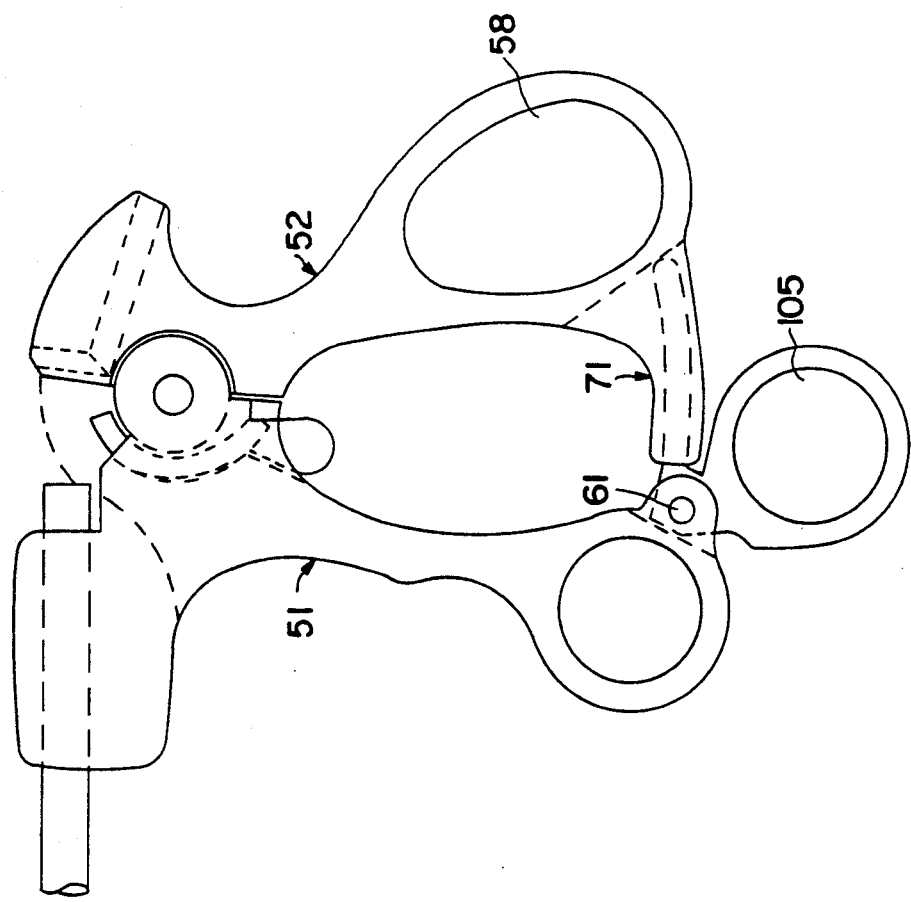

FIGS. 21 and 22 additionally show that, instead of a finger hollow on the lever limb 68, a gripping lug 105 is provided, movement of the lever limb 68 both forwards and backwards thereby being possible without relocating the finger.

I claim:

1. A surgical instrument having closable jaws, comprising: a pull element having a pivot on one end thereof and at least one limb member at the opposite end; jaw pats fixed on the pull element, at least one jaw part forming an axis of rotation with the pull element and being arranged rotatably about this axis of rotation; a shank tube, with the pull element passing through the shank tube; a first recess formed in at least one movable jaw part, the center point of which rotates about the pivot on the pull element; an annular piece provided in the shank tube at least partly surrounded by the first recess in the use position; wherein at least one jaw part rotates about the annular piece during its closing or opening movement; and wherein, the pull element protrudes form the shank tube at the other end thereof and is fixed releasably on a neck of a limb member.

2. A surgical instrument as claimed in claim 1 wherein the first recess is of approximately semicircular design and forms at least one guiding limb which engages in a mating recess selected from the group consisting of an opening and a groove.

3. A surgical instrument as claimed in claim 2 wherein the pull element includes a fork having two fork limbs which accommodate between them said at least one guiding limb.

4. A surgical instrument as claimed in claim 3 wherein a pin passes through said fork and guiding limbs as a pivot.

5. A surgical instrument as claimed in claim 2 wherein the pivot is a hinge pin and wherein one of the jaw parts is a shaft jaw part, the said fixed jaw part having a recess for accommodating the guiding limb of the movable jaw part which is connected in the fixed jaw part recess via the hinge pin to the fixed jaw part.

6. A surgical instrument as claimed in claim 2 wherein the shank tube has a rim, and the annular piece is of approximately semicircular design, and the shank tube rim forms a funnel-shaped constriction by means of a draw-in wall, and towards the mating recess forms a funnel-shaped enlargement by means of a sliding edge.

7. A surgical instrument as claimed in claim 6 wherein the center point of the annular piece and the center point of the first recess coincide or lie close together in the use position, the radius of the annular piece being slightly less than the radius of the first recess.

8. A surgical instrument as claimed in claim 1 wherein the annular piece comprises two disk-shaped elements between which is arranged a pivot pin which, in the use position, rests in a blind slot-like recess while the disk-shaped elements are accommodated by cut-outs in the jaw parts.

9. A surgical instrument as claimed in claim 2 wherein a guide clip is placed on the shank tube, said guide clip forming two hoops between which the jaw parts are accommodated, the guide clip serving for the centering of the guiding limbs relative to the mating recess.

10. A surgical instrument as claimed in claim 9 wherein the two hoops are connected to one another via snap-in strips which have snap-in knobs which snap into the mating recess in the use position.

11. A surgical instrument as claimed in claim 1 wherein, on the pull element, there is a plunger piece in which is formed at least one guiding groove which interacts with a guiding projection in the shank tube.

12. A surgical instrument as claimed in claim 1 wherein said limb member is a forceps first limb.

13. A surgical instrument as claimed in claim 12 wherein fixed on the pull element is a driving ball which rests in a ball socket in said neck in the use position.

14. A surgical instrument as claimed in claim 12 wherein the shank tube is secured on a holding device which is part of a forceps second limb which is connected to the forceps first limb via a pivot.

15. A surgical instrument as claimed in claim 14 wherein on the forceps second limb is a catch device which limits the movement of one forceps limb in relation to the other forceps limb.

16. A surgical instrument as claimed in claim 15 wherein provided in the forceps second limb is a guiding channel for a semicircular arch which rotates about the pivot connected to the forceps first limb and, in an end position, projects with a stop stud beyond a stop face.

17. A surgical instrument as claimed in claim 16 wherein in the said end position the semicircular arch engages releasably behind a latching heel.

18. A surgical instrument as claimed in claim 1 having two limb members which are connected to one another in an articulated fashion via a limb member pivot, and having a locking device which faces the two limbs in relation to one another, the locking device having a locking strip which is connected in articulated fashion to one limb and is operatively connected via locking teeth to at least one engagement tooth on the other limb, wherein adjoining the locking strip is a lever limb with a holding means.

19. A surgical instrument as claimed in claim 18 wherein the lever limb projects downwards approximately at right angles from the locking strip.

20. A surgical instrument as claimed in claim 18 wherein the locking strip is held in engagement with at least one engagement tooth under the pressure of an energy accumulator.

21. A surgical instrument as claimed in claim 18 wherein adjoining the locking strip is a hook which is connected to one limb with a hinge pin.

22. A surgical instrument as claimed in claim 21 wherein the hook rests in a recess in one limb.

23. A surgical instrument as claimed in claim 21 wherein the hook forms with the locking strip an engagement hollow into which an energy accumulator designed as a spring strip engages.

24. A surgical instrument as claimed in claim 23 wherein, towards the spring strip the hook forms a front face against which the spring strip rests.

25. A surgical instrument as claimed in claim 18 wherein the locking strip is assigned a receiver on the other limb.

26. A surgical instrument as claimed in claim 25 wherein the receiver comprises two clamp strips, the inner faces of which are covered with latching teeth which interact with latching teeth on the locking strip.

27. A surgical instrument as claimed in claim 26 wherein the clamp strips form an internal shape of oval cross-section into which the locking strip engages, and wherein the locking strip is also of oval cross-section.

* * * * *